United States Patent
Lueckel et al.

(10) Patent No.: US 10,485,641 B2
(45) Date of Patent: Nov. 26, 2019

(54) PERSONAL HYGIENE DEVICE AND METHOD OF CONTROLLING A PERSONAL HYGIENE DEVICE

(71) Applicant: Braun GmbH, Kronberg (DE)

(72) Inventors: Kris Lueckel, Koenigstein (DE); Kervin Heinrich Küchler, Darmstadt (DE); Egle Kiiver, Bad Soden (DE)

(73) Assignee: BRAUN GMBH, Kronberg (DE)

( * ) Notice: Subject to any disclaimer, the term of this patent is extended or adjusted under 35 U.S.C. 154(b) by 336 days.

(21) Appl. No.: 15/293,713

(22) Filed: Oct. 14, 2016

(65) Prior Publication Data

US 2017/0105823 A1   Apr. 20, 2017

(30) Foreign Application Priority Data

Oct. 16, 2015 (EP) .................................. 15190167

(51) Int. Cl.
| | |
|---|---|
| A61C 17/22 | (2006.01) |
| A46B 5/00 | (2006.01) |
| A46B 9/04 | (2006.01) |
| A46B 15/00 | (2006.01) |
| A61C 17/34 | (2006.01) |

(Continued)

(52) U.S. Cl.
CPC .......... *A61C 17/221* (2013.01); *A46B 5/0095* (2013.01); *A46B 9/04* (2013.01); *A46B 15/0012* (2013.01); *A61C 17/224* (2013.01); *A61C 17/225* (2013.01); *A61C 17/34* (2013.01); *B26B 19/3873* (2013.01); *A61C 15/047* (2013.01); *B26B 19/388* (2013.01)

(58) Field of Classification Search
None
See application file for complete search history.

(56) References Cited

U.S. PATENT DOCUMENTS

| | | |
|---|---|---|
| 4,703,247 A | 1/1987 | Moriaka |
| 5,619,126 A | 4/1997 | Lang |
| 5,623,193 A | 4/1997 | Lang et al. |

(Continued)

FOREIGN PATENT DOCUMENTS

| | | |
|---|---|---|
| EP | 0605438 | 7/1994 |
| JP | H04236979 | 8/1992 |

(Continued)

OTHER PUBLICATIONS

European Search Report; dated Mar. 22, 2016; 5 pages.

*Primary Examiner* — Bickey Dhakal
(74) *Attorney, Agent, or Firm* — Vladimir Vitenberg

(57) ABSTRACT

A personal hygiene device has a drive unit, an energy storage, such as a rechargeable battery, a determination unit for repeatedly or constantly determining an energy storage level of the energy storage, and a control unit arranged for providing energy from the energy storage at the drive unit during an on state of the device and for gradually reducing the energy level from a nominal energy level to a first reduced energy level during a first energy level reduction time period when the determined energy storage level has fallen below a first energy storage level threshold but is above a second energy storage level threshold and for continuing provision of the first reduced energy level while the device stays in an on state and the determined energy storage level stays above the second energy storage level threshold.

12 Claims, 3 Drawing Sheets

(51) Int. Cl.
*B26B 19/38* (2006.01)
*A61C 15/04* (2006.01)

(56) References Cited

U.S. PATENT DOCUMENTS

| | | | |
|---|---|---|---|
| 5,973,497 A | 10/1999 | Bergk et al. | |
| 6,646,400 B2 * | 11/2003 | Uno | B62M 6/45 |
| | | | 315/78 |
| 7,336,048 B2 | 2/2008 | Lohr | |
| 8,198,866 B2 | 6/2012 | Vetter | |
| 8,963,458 B2 | 2/2015 | Muto et al. | |
| 9,717,325 B2 * | 8/2017 | Mongan | A46B 17/06 |
| 10,084,401 B2 * | 9/2018 | Godlieb | H02P 7/29 |
| 2003/0096158 A1 | 5/2003 | Takano et al. | |
| 2012/0024552 A1 * | 2/2012 | Kawano | A01D 69/02 |
| | | | 173/2 |
| 2012/0066848 A1 * | 3/2012 | Klemm | A61C 17/221 |
| | | | 15/21.1 |
| 2017/0197520 A1 * | 7/2017 | Schindler | B60L 58/18 |

FOREIGN PATENT DOCUMENTS

| | | |
|---|---|---|
| JP | H08849 | 1/1996 |
| JP | 2003319564 | 11/2003 |

\* cited by examiner

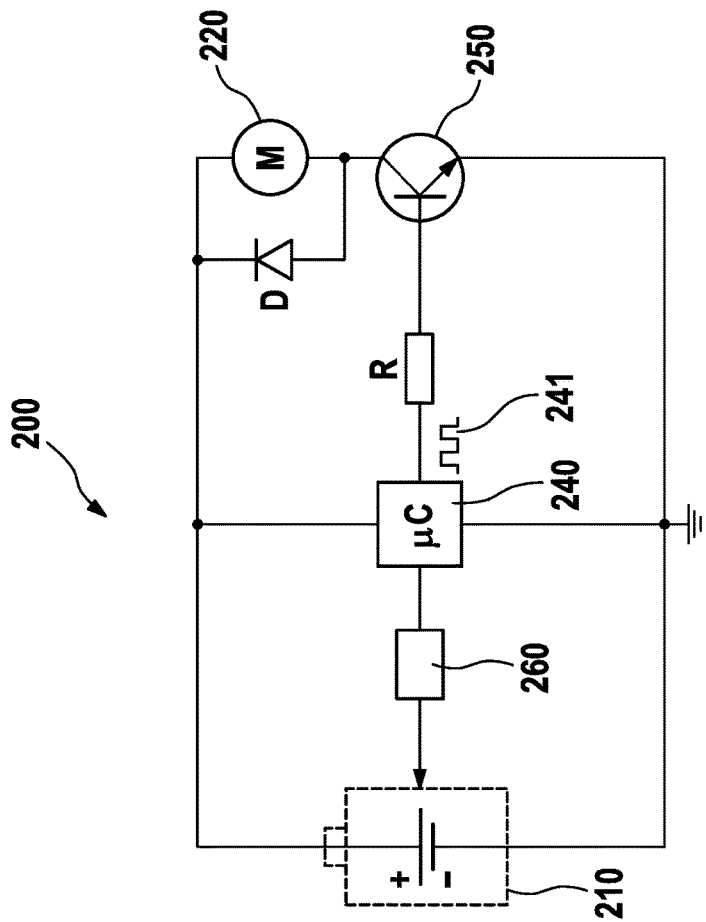
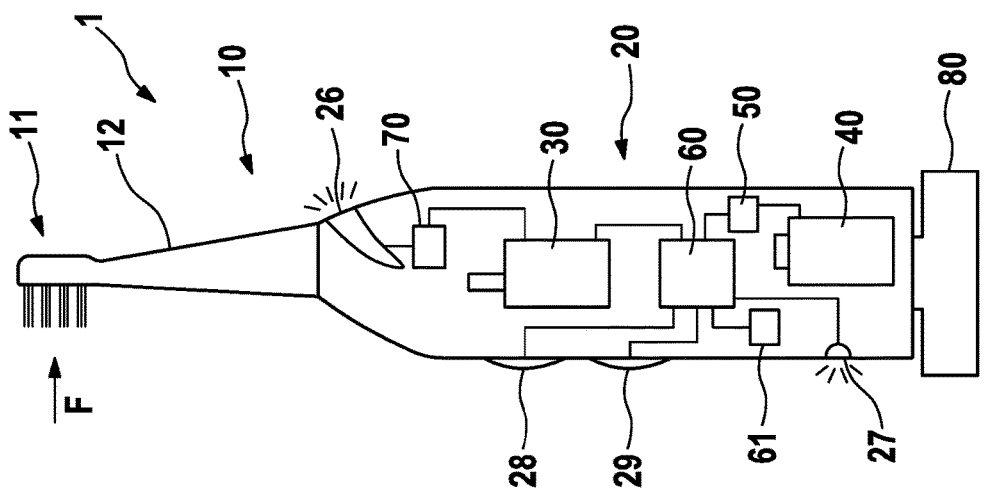

PERSONAL HYGIENE DEVICE AND METHOD OF CONTROLLING A PERSONAL HYGIENE DEVICE

FIELD OF THE INVENTION

The present invention is concerned with a personal hygiene device comprising an energy storage, a drive unit, and a control unit for providing energy from the energy storage at the drive unit. The present invention is further concerned with a method of controlling such a personal hygiene device.

BACKGROUND OF THE INVENTION

It is known that a personal hygiene device comprising an energy storage such as a rechargeable battery and a drive unit to which energy is supplied from the energy storage may be controlled such that the drive unit is reduced to zero speed once a low charging state of the rechargeable battery is determined.

It is an object of the present disclosure to provide a personal hygiene device that is improved over the known personal hygiene devices, in particular wherein the personal hygiene device is arranged to communicate a low energy storage level to a user in an easily comprehensible manner.

SUMMARY OF THE INVENTION

In accordance with one aspect there is provided a personal hygiene device comprising a drive unit, an energy storage, in particular a rechargeable battery, a determination unit for repeatedly or constantly determining an energy storage level of the energy storage, and a control unit arranged for providing energy from the energy storage at the drive unit during an on state of the personal hygiene device and for gradually reducing the energy level provided at the drive unit from a nominal energy level to a first reduced energy level during a first energy level reduction time period when the determined energy storage level has fallen below a first energy storage level threshold but is above a second energy storage level threshold and for continuing provision of the first reduced energy level while the personal hygiene device stays in an on state and the determined energy storage level stays above the second energy storage level threshold.

In accordance with one aspect there is provided a personal hygiene device comprising a drive unit, in particular comprising a DC motor, an energy storage, and a control unit arranged for providing energy from the energy storage at the drive unit during an on state of the personal hygiene device and for gradually increasing the energy level provided at the drive unit from a start energy level to a nominal energy level during a first energy increase time period when the personal hygiene device is switched from an off state into the on state, in particular wherein the start energy level is in a range of between 10% and 90% of the nominal energy level.

In accordance with one aspect there is provided a method of controlling a personal hygiene device having a drive unit, an energy storage, and a control unit comprising the steps of:
changing the personal hygiene device from an off state into an on state;
repeatedly or constantly determining the energy storage level of the energy storage;
gradually reducing an energy level provided at the drive unit from a nominal energy level to a first reduced energy level during a first energy level reduction time period if the determined energy storage level falls below a first energy storage level threshold but is above a second energy storage level threshold; and
continuingly providing the first reduced energy level while the personal hygiene device stays in the on state and the determined energy storage level stays above the second energy storage level threshold.

BRIEF DESCRIPTION OF THE DRAWINGS

The present description is further elucidated by a detailed description of embodiments of the proposed personal hygiene device and the proposed method of controlling a personal hygiene device. In the following description reference is made to figures, where FIG. 1 is a schematic depiction of a personal hygiene device in accordance with the present description;

FIG. 2 is a simplified depiction of a circuit comprising energy storage, drive unit, determination unit, and control unit of a proposed personal hygiene device;

DETAILED DESCRIPTION OF THE INVENTION

Figure 3:
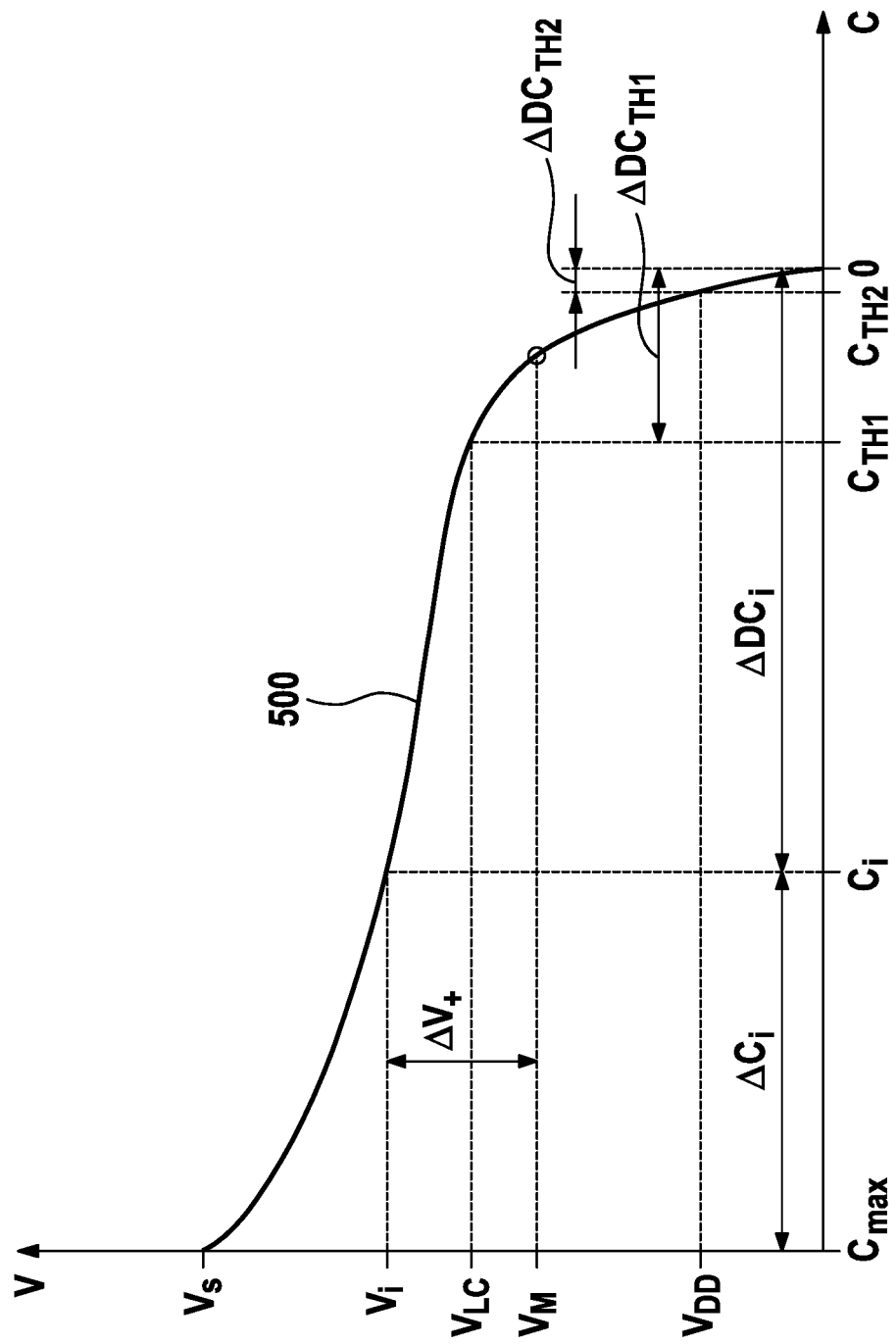
FIG. 3 is a schematic depiction of an example voltage curve (the voltage being a measure of an energy storage level) of a rechargeable battery versus the energy storage capacity.

In accordance with the present disclosure, a personal hygiene device as proposed comprises a control unit that reduces the energy level supplied at a drive unit once a determination unit detects that the energy storage level of an energy storage (such as a rechargeable battery) has fallen below a first energy storage level threshold. While here the term "energy level" is used, this shall encompass the provision of a (average) voltage level at the drive unit and the actual energy level will then result from the (average) voltage and the current that flows through the drive unit. This reduction from a nominal energy level to a first reduced energy level occurs during a first energy level reduction time period. Both, the reduction and the time period during which it occurs may be set to values such that the energy level reduction is readily noticeable to a user of the personal hygiene device, while the user should still be able to conclude the current use of the personal hygiene device before the energy storage needs to be recharged (i.e. the first energy storage level threshold should relate to a remaining discharge capacity of the energy storage that allows using the personal hygiene device for at least a typical usage period). This energy level reduction is also called a ramp-down of the energy level. The first reduced energy level may lie be in a range of between about 80% to 90% of the nominal energy level, even though this shall not be considered as limiting and a skilled person may choose any suitable value such as 10%, 15%, 20%, 25%, 30%, 35%, 40%, 45%, 50%, 55%, 60%, 65%, 70%, 75%, or 95% or any other intermediate value.

In some embodiments, the control unit also reduces the energy level provided at the drive unit from the nominal level to the first reduced energy level within a second energy level reduction time period (which may be identical or different in length than the first energy level reduction time period) essentially after the personal hygiene device is switched on and in case that the first reduced energy level had been provided in the previous on-state of the personal hygiene device and a charging of the energy storage has not meanwhile happened. The control unit may use a flag stored in a memory unit in order to recognize a previous application of the first reduced energy level and the flag may be deleted by the control unit in case the energy storage is sufficiently charged. The control unit may be arranged to wait for a nominal energy level time period before it ramps down the energy level after the personal hygiene device is switched on again, so that the ramp-down is even more noticeable to the user. The control unit may be arranged to directly apply the first reduced energy level in case that a switch-off time period between the two successive on-states was below a first switch-off time period threshold, which first switch-off time period threshold may lie in a range of between 1 second and 600 seconds, even though this shall not be considered as limiting.

In some embodiments, the control unit is arranged to ramp-down the energy level provided at the drive unit from the first reduced energy level to a second reduced energy level or zero energy level during a third energy level reduction time period if the energy storage level of the energy storage falls below a second energy storage level threshold. This should avoid that the energy storage gets deep discharged.

In accordance with an independent aspect of the present disclosure, a control unit of a personal hygiene device is arranged to increase an energy level provided at a drive unit immediately after the personal hygiene device has been switched on from a start energy level to a nominal energy level. This independent aspect of a ramp-up of the energy level may be combined with one or several features of the ramp-down of the energy level described herein (e.g. the ramp-down as described may additionally include the ramp-up). A ramp-up may not be performed when a switch-off time period between two successive on states of the personal hygiene device was below a first switch-off time period threshold, which may be chosen to lie in a range of between 1 second and 600 seconds, in particular around 30 seconds.

The personal hygiene device may have at least two different modes and the ramp-down (and/or the ramp-up) may be deactivated in one of the at least two modes. E.g. one mode may include a varying energy provision at the drive unit, in which mode the ramp-down (and/or the ramp-up) is deactivated. The personal hygiene device may comprise at least one indicator element for indication that the energy storage level of the energy storage has fallen below the first energy storage level threshold. The indicator element may use visual, audible, or tactile means in order to indicate the low charge state.

The control unit may provide the energy level at the drive unit by means of a pulse width modulation (PWM) signal, by which the voltage provided from an energy storage such as a rechargeable battery, e.g. a lithium ion accumulator, is applied at the drive unit. An average voltage is then applied at the drive unit that is depending on the current voltage level provided by the energy storage and the duty cycle, i.e. the ratio of "on" time of the PWM signal vs the regular time period of the PWM. E.g. the PWM signal may control a switch that connects and disconnects the energy storage with the drive unit. The duty cycle of the PWM may in particular be controllable so that a constant average voltage can be provided at the drive unit despite a changing voltage provided by the energy storage while it is discharged. In some embodiments, the control unit may be realized by a microcontroller such as the CC2541 from Texas Instruments, Dallas, Tex., USA. The microcontroller may provide the PWM signal with a frequency of 16 kHz, even though this is not to be considered as limiting and any other suitable frequency may be chosen. In some embodiments, the frequency of the PWM signal is variable.

The drive unit may comprise a DC motor such as a FK-180 SH-2848 from Mabuchi Motor KK, Matsudo, Japan. In some embodiments, the drive unit comprises a resonant motor. While a reduction of the energy level provided at a DC motor leads to a frequency reduction (i.e. speed reduction) of the motor rotation (the motor speed is proportional to the back electromagnetic force, so the motor speed may not necessarily follow the same curve as the energy level (or voltage level) that is provided at the drive unit), the reduction of the energy level at a resonant motor essentially leads to a reduction of the motor amplitude.

A personal hygiene device in accordance with the present disclosure shall encompass in particular oral hygiene device such as electric toothbrushes, electric flossers or electric interdental cleaners, electric tongue cleaners, electric gum massagers etc. The term personal hygiene device shall further encompass skin or body hygiene devices such as electric shavers or electric depilators, electric skin treatment devices (e.g. electric massagers or electric skin peeling devices).

FIG. 1 is a schematic depiction of a personal hygiene device 1 that is here realized as an electric toothbrush. The personal hygiene device 1 has a head section 10 and a handle section 20 that has a handle housing 21 suitable for being gripped by a human user. The head section 10 comprises a functional head 11, which may be mounted for motion with respect to a housing 12 of the handle section. In some embodiments, the head section 10 may be repeatedly detachable and attachable to the handle section 20 so as to allow attaching different head sections for different treatments or different head sections for different users or to simply replace a worn-out head section by a new head section. The personal hygiene device 1 is here shown as placed on a charger stand 80 on which an energy storage 40 of the personal hygiene device may be (re-)charged. In accordance with the present disclosure, the personal hygiene device 1 comprises an energy storage 40, a drive unit 30, a determination unit 50 arranged for repeatedly or continuously (at least during the on-state of the personal hygiene device 1) determining the energy storage level of the energy storage, and a control unit 60 arranged for controlling the provision of energy from the energy storage 40 at the drive unit 30. The control unit 60 may comprise a memory unit 61 for e.g. storing a flag that indicates that the determination unit 50 had detected that the energy storage level of the energy storage has fallen below a first energy storage level threshold. The flag may be erased by the control unit 60 once the energy storage has been sufficiently recharged. The drive unit 30 may in particular comprise a DC motor. The drive unit 30 may further comprise a gear to convert the motion provided by a motor to a different motion, e.g. in order to convert a continuously rotating motion provided by a motor shaft into an oscillatory rotating motion of an output shaft, which output shaft may then be coupled with the head section 10 for driving either the whole head section 1 into a motion or for driving only the functional head 11 into a motion.

The handle section 20 may further comprise one or several of the following features:
- a pressure indicator 26 that may be controlled to indicate that a force F applied at a functional head 11 is above a first pressure threshold (the personal hygiene device 1 may in particular comprise a pressure detection unit 70 arranged for (indirectly or directly) measuring the pressure applied at the functional head 11);
- a low-charge indicator element 27 for indicating in a visual or audible manner a detected low charge state of the energy storage 40;
- an on/off switch 28 for switching the personal hygiene device from an off state into an on state and vice versa (in some embodiments, the personal hygiene device may be automatically switched on and off based on an e.g. capacitive detection of tissue being close to the head section); and/or a mode selector 29 for switching the personal hygiene device 1 from a first mode into a second mode, where the personal hygiene device 1 may have any number of different modes, e.g. two modes, three modes, four modes etc.

FIG. 2 is a schematic depiction of a circuitry 200 comprising an energy storage 210, a drive unit 220, a control unit 240, and a determination unit 250 as previously described. The energy storage 210 (e.g. a rechargeable battery such as a Lithium-Ion battery or a NiMH battery) is arranged so that the energy storage voltage can be applied at the drive unit 220 when a switch 250 (which may be realized as a transistor or a MOSFET) is closed. The switch 250 is controlled by the control unit 240 that provides a pulse width modulation (PWM) signal 241 at an in particular fixed PWM frequency. The determination unit 250 is arranged to repeatedly or continuously measure an energy storage level of the energy storage 210, e.g. the determination unit 250 may determine the energy storage voltage (e.g. the open circuit voltage) in order to determine the remaining discharge capacity of the energy storage (the discharge capacity is a measure of the energy storage level).

The control unit 240 may be arranged to provide a PWM signal 241 having a constant duty cycle while the energy storage level of the energy storage 210 is above a first energy storage level threshold in order to provide a nominal energy level, which nominal energy level may then slightly decrease over time as the battery voltage will drop when the energy storage 210 is discharged. In some embodiments, the control unit 240 is arranged to compensate for the dropping energy storage voltage over time by respectively increasing the duty cycle of the PWM signal 241. Then, the nominal energy level stays constant over time.

Once the determination unit 250 detects that the energy storage level of the energy storage 210 falls below a first energy storage level threshold, the control unit 240 is arranged to reduce the duty cycle of the PWM signal 241 over a first energy level reduction time period so that the energy level provided at the drive unit 220 is reduced from the nominal energy level to a first reduced energy level. As a result, the drive unit 220 will, e.g., rotate at a lower rotation frequency. The reduction in the energy level provided at the drive unit 220 may be set such that the typical use of the personal hygiene device in which the circuitry 200 is implemented can be continued, but also such that the consumer notices on the one hand the reduction phase and also the reduced power of the personal hygiene device. This should then trigger the user to recharge the energy storage by, e.g., putting the personal hygiene device onto a charger unit or replacing the discharged energy storage by a charged energy storage.

FIG. 3 is a schematic depiction of a discharge curve 500 of an energy storage, e.g. a rechargeable Lithium-Ion accumulator, where the voltage V of the energy storage (the voltage may be measured in volt) is plotted versus the capacity C of the energy storage (the capacity C may be measured in milli-ampere hours). The voltage of the energy storage generally decreases constantly during the discharging of the energy storage. The energy storage has voltage $V_s$ when it is fully charged, which is the state when the energy storage has the ability to discharge its maximum capacity $C_{max}$, and has a voltage $V_i$ after a charge amount $\Delta C_i$ had been discharged from the energy storage. The energy storage voltage $V_i$ is thus a direct measure of the remaining discharge capacity $\Delta DC_i$. In the shown example discharge curve 500, the voltage of the energy storage breaks down rather abruptly when the remaining discharge capacity $\Delta DC_i$ reaches a certain threshold discharge capacity $\Delta DC_{TH2}$ (relating to capacity $C_{TH2}$ and energy storage voltage $V_{DD}$). One may thus define that a certain remaining discharge capacity $\Delta DC_{TH1}$ (relating to capacity $C_{TH2}$ and energy storage voltage $V_{LC}$), that is larger than the threshold capacity $\Delta DC_{TH2}$, is an indicator that the energy storage has a low charge state that should be indicated to the user of the device in which the energy storage is used. The determination unit discussed before may thus be arranged to measure the current energy storage voltage and in case the measured voltage drops below $V_{LC}$, this indicates that the energy storage level has fallen below a first energy storage level threshold leading to a controlled reduction of the energy level provided at the drive unit from a nominal energy level to a first reduced energy level. In case the measured voltage drops below $V_{DD}$, this indicates that the energy storage level has fallen below a second energy storage level threshold and the personal hygiene device may then in particular be shut down to avoid that the energy storage is deep discharged.

The energy level provided at the drive unit is influenced by the energy storage voltage that is applied at the drive unit. In order to overcome the issue of a constantly dropping voltage of the energy storage, the control unit may be arranged to apply an average voltage $V_M$ at the drive unit. The voltage $V_M$ may be set at a voltage value that is lower than the low charge voltage $V_{LC}$ so that until the low charge detection always the average voltage $V_M$ can be provided. As has been described before, the control unit may provide the current energy storage voltage $V_i$ in a PWM manner at the drive unit, where the duty cycle of the PWM is given (in percent of the regular PWM time period) by $V_M/(\Delta V_+ + V_M)$—where $\Delta V_+ = V_i - V_M$, i.e. by the ratio between the chosen voltage $V_M$ and the current energy storage voltage $V_i$.

Figure 4C:
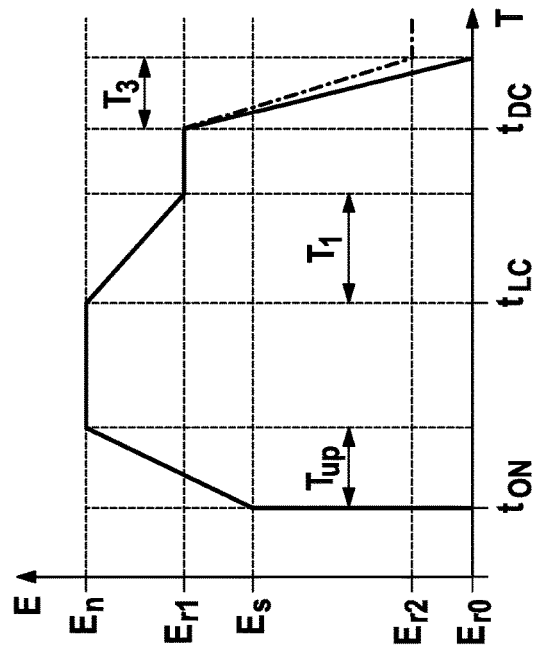
FIG. 4C is a third example depiction of the energy level provided at a drive unit over time in accordance with the present description.
Figure 4A:
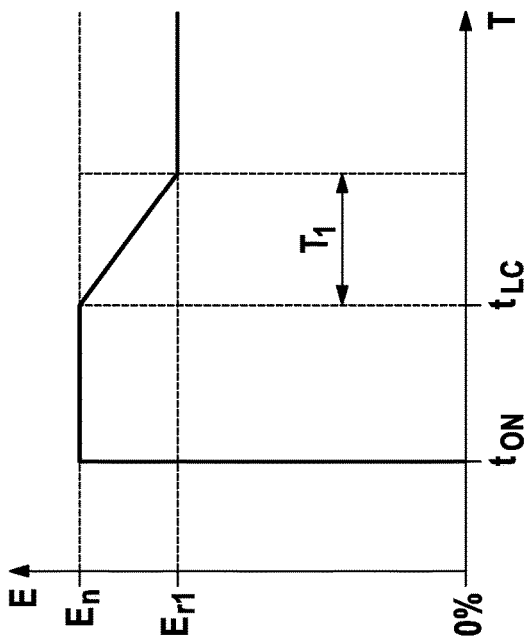
FIG. 4A is a first example depiction of the energy level provided at a drive unit over time in accordance with the present description.

FIG. 4A is a diagram showing the energy level E (given in percent of a nominal energy level $E_n$) that is provided (by the control unit) at the drive unit over time t for a first example activity sequence. Here, the personal hygiene device is first in the off-state and is switched into the on-state at time instant $t_{ON}$. While the personal hygiene device is in the on-state, the determination unit repeatedly or continuously determines the energy storage level of the energy storage. At time instant $t_{LC}$ the determination units here detects that the energy storage level of the energy storage has fallen below a first energy storage level threshold (low charge detection). In accordance with the present description, the control unit than reduces the energy level that is applied at the drive unit from the nominal energy level $E_n$ ($E_n$=100%) to a first reduced energy level $E_{r1}$ ($E_{r1}$=(100−X)%), where X may be any number between 1 and 99, but in particular X may be in the range of between 10 and 20, so that the personal hygiene device can still be operated, but provides its function with reduced "power", which reduced power is noticeable by the user and is strong enough to trigger the user to consider recharging the personal hygiene device (or to replace the depleted energy storage) once the current treatment session is completed. The control unit reduces the energy level provided at the drive unit from the nominal energy level $E_n$ to the first reduced energy level $E_{r1}$ during a first energy level reduction time period $T_1$. The first energy level reduction time period $T_1$ may have any suitable length, but the first energy level reduction time period $T_1$ should on the one hand be long enough to be noticeable by the user and on the other hand should not be too distracting to the user. Hence, the first energy level reduction time period $T_1$ may be in a range of between 0.5 seconds and 10 seconds, in particular in a range of between 2 seconds and 8 seconds, and further in particular of about 5 seconds.

Figure 4B:
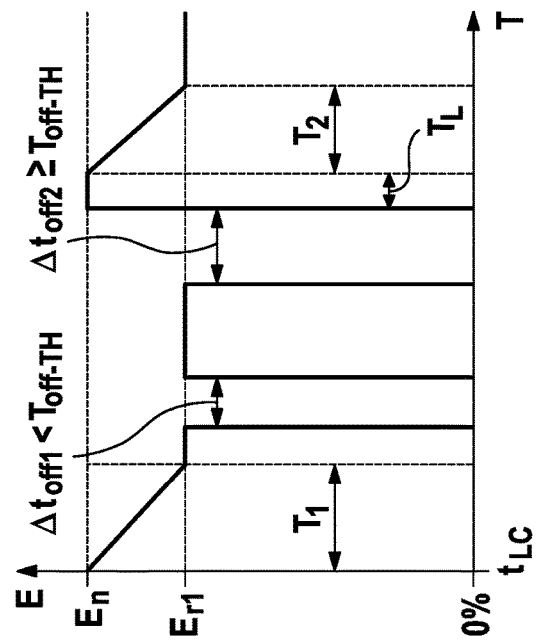
FIG. 4B is a second example depiction of the energy level provided at a drive unit over time in accordance with the present description.

FIG. 4B is a diagram showing the energy level E (given in percent of the nominal energy level $E_n$) that is provided (by the control unit) at the drive unit over time t for a second example activity sequence. Here, the personal hygiene device is in the on-state at the beginning of the sequence and the low charge detection has just happened at time instant $t_{LC}$. As described for FIG. 4A, the control unit then reduces the energy level provided at the drive unit from the nominal energy level $E_n$ ($E_n$=100%) to the first reduced energy level $E_{r1}$ ($E_{r1}$=(100−X)%) during the first energy level reduction time period $T_1$. The personal hygiene device is then switched into the off-state at time instant $t_{off1}$. The personal hygiene device is kept in the off-state for a switch-off time period $\Delta t_{off1}$ that is smaller than a first switch-off time period threshold $T_{off-TH}$, i.e. $\Delta t_{off1} < T_{off-TH}$. The first switch-off time period threshold $T_{off-TH}$ may be set to a value that is typical for users that switch off the personal hygiene device during a treatment session in order to do something else, e.g. responding to a family member or cleaning a functional head of the personal hygiene device. The first switch-off time period threshold $T_{off-TH}$ may be any suitable time period, e.g. between 1 second and 600 seconds, but may in some examples be set to be about 30 seconds. After the short switch-off time period $\Delta t_{off1}$, the personal hygiene device is switched on again at time instant $t_{on1}$. The control unit now immediately provides the first reduced energy level $E_{r1}$ at the drive unit as a consequence of the short switch-off time period $\Delta t_{off1}$. At time instant $t_{off2}$ the personal hygiene device is switched off again. The personal hygiene device is kept in the off-state for a switch-off time period $\Delta t_{off2}$ that is equal to or higher than the first switch-off time period threshold $T_{off-TH}$, i.e. $\Delta t_{off1} \geq T_{off-TH}$. The personal hygiene device is then switched on again at time instant $t_{on2}$. The control unit then provides the nominal energy level $E_n$ at the drive unit and may immediately reduce the energy level provided at the drive unit from the nominal energy level $E_n$ to the first reduced energy level $E_{r1}$ during a second energy level reduction time period $T_2$. The second energy level reduction time period $T_2$ may identical in length as the first energy level reduction time period $T_1$ or may have another suitable value, where the second energy level reduction time period $T_2$ may in particular have a length in a range of between 0.5 seconds and 10 seconds. Instead of directly reducing the energy level from the nominal energy level $E_n$ to the first reduced energy level $E_{r1}$, the control unit may be arranged to wait a nominal energy level time period $T_L$ until it reduces the energy level. Such a (short) nominal energy level time period $T_L$ may make the reduction even more noticeable to the user. The nominal energy level time period $T_L$ may in particular have a length in a range of between 0.5 seconds and 10 seconds.

The control unit may store a flag or any other information in a memory unit, which flag or information is an indicator that an energy storage level below a first energy storage level threshold had been detected (low charge detection). This flag may then be erased from the memory unit once the control unit determines that a sufficient charging of the energy storage has happened. Thus, after a switch-off period, the control unit may check the status of the flag once the personal hygiene device is switched on. If the flag indicating the low charge detection is still stored, then the control unit may (immediately or after reducing the energy level from the nominal energy level to the first reduced energy level, depending on the length of the switch-off period) provide the first reduced energy level at the drive unit independent from the outcome of the energy storage level detection, as the energy storage may have recovered slightly during the switch-off period and the energy storage level detection may then indicate an energy storage level above the first energy storage level threshold for a certain time period.

FIG. 4C is a diagram showing the energy level E (given in percent of the nominal energy level $E_n$) that is provided (by the control unit) at the drive unit over time t for a third example activity sequence. Here, the personal hygiene device is in the off-state at the beginning of the sequence. The personal hygiene device is then switched into the on-state at time instant $t_{on}$. In this third example sequence, the control unit is arranged to provide a start energy level $E_s$ ($E_s$=(100−Y)%) at the drive unit once the personal hygiene device is switched on and to increase the energy level from the start energy level $E_s$ to the nominal energy level $E_n$ during a first energy level increase time period $T_{up}$. The first energy level increase time period $T_L$ may in particular have a length in a range of between 0.1 seconds and 10 seconds, in particular in a range of between 0.25 seconds and 2 seconds, further in particular of about 0.75 seconds. A fast energy increase ensures that the device is on its nominal level within a short time. The start energy level $E_s$ may have any suitable value, but the start energy level $E_s$ may in particular be in a range of between 10% and 90% of the nominal energy level $E_n$ (i.e. Y is in between 90 and 10). In some embodiments, the start energy level $E_s$ is about 50% of the nominal energy level $E_n$. Such a "ramp-up" phase slowly increases the sound of the personal hygiene device from a medium level to the nominal sound level, which procedure was discovered as being pleasant for users, in particular in embodiments where the drive unit comprises a DC motor and thus the sound of the personal hygiene device starts at a medium frequency (e.g. comprising a 50 Hz sound peak due to the frequency of the DC motor), which then rises to a nominal sound having a nominal higher frequency sound peak in the range of e.g. between 75 Hz and 100 Hz, even though the frequencies mentioned here are just examples and should not be considered as limiting the scope of the disclosure.

It is noted that a personal hygiene device having a drive unit, in particular comprising a DC motor, an energy storage, and a control unit arranged for providing energy from the energy storage at the drive unit during an on state of the personal hygiene device and for gradually increasing the energy level provided at the drive unit from a start energy level to a nominal energy level during a first energy increase time period when the personal hygiene device is switched from an off state into the on state, in particular wherein the start energy level is in a range of between 10% and 90% of the nominal energy level, is considered an independent aspect of the present disclosure.

As is further depicted in FIG. 4C, the nominal energy level $E_n$ is then provided until the determination unit determines a low energy storage level at time instant $t_{LC}$. Then, as had been described before, the control unit reduces the energy level provided at the drive unit from the nominal energy level $E_n$ to the first reduced energy level $E_{r1}$ during the first energy level reduction time period $T_1$. The first reduced energy level $E_{r1}$ is then provided at the drive unit until the determination unit determines at time instant $t_{DC}$ that the energy storage level of the energy storage has fallen below a second energy storage level threshold indicating a depletion of the energy storage. The control unit is then reducing the energy level provided at the drive unit from the first reduced energy level $E_{r1}$ to either zero energy level $E_{r0}$ ($E_{r0}$=0%) or to a second reduced energy level $E_{r2}$ ($E_{r2}$=(100−Z)%) during a third energy level reduction time period $T_3$. The third energy level reduction time period $T_3$ may in particular have a length in a range of between 1 second to 240 seconds, in particular in a range of between 5 seconds and 60 seconds, and further in particular of about 30 seconds. In some embodiments, the energy level is reduced to zero energy level as this avoids that the energy storage becomes deep discharged.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal hygiene device comprising:
   a drive unit;
   an energy storage comprising a rechargeable battery;
   a determination unit for repeatedly or constantly determining an energy storage level of the energy storage;
   a control unit arranged for providing energy from the energy storage at the drive unit during an on state of the personal hygiene device and for gradually reducing the energy level provided at the drive unit from a nominal energy level to a first reduced energy level during a first energy level reduction time period when the determined energy storage level has fallen below a first energy storage level threshold but is above a second energy storage level threshold and for continuing provision of the first reduced energy level while the personal hygiene device stays in an on state and the determined energy storage level stays above the second energy storage level threshold,
   wherein the control unit directly provides the first reduced energy level at the drive unit when a switch-off time period of the drive unit has been lower than a first switch-off time period threshold and the first reduced energy level had been provided at the drive unit in the preceding on-state of the personal hygiene device, wherein the first switch-off time period threshold is between 1 second and 600 seconds.

2. The personal hygiene device in accordance with claim 1, wherein the control unit is arranged for gradually reducing the energy level provided at the drive unit from the nominal energy level to the first reduced energy level during a second energy level reduction time period essentially immediately after the personal hygiene device is changed from an off state into an on state when the first reduced energy level had been provided in the preceding on-state of the personal hygiene device and a charging of the energy storage had not meanwhile happened.

3. The personal hygiene device in accordance with claim 2, wherein the control unit is arranged to reduce the provided energy level only after a nominal energy level time period after the on state was initiated, where the nominal energy level time period is between 0.5 seconds and 10 seconds.

4. The personal hygiene device in accordance with claim 1, wherein the control unit is arranged for gradually reducing the energy level provided at the drive unit from the first reduced energy level to a second reduced energy level or to zero energy level during a third energy level reduction time period when the determined energy storage level has fallen below the second energy storage level threshold.

5. The personal hygiene device in accordance with claim 1, wherein the drive unit comprises a DC motor.

6. The personal hygiene device in accordance with claim 1, wherein the first reduced energy level is between 80% and 90% of the nominal energy level.

7. The personal hygiene device in accordance with claim 1, wherein the first reduction time period or the second reduction time period is between 0.5 seconds and 10 seconds.

8. The personal hygiene device in accordance with claim 1, wherein the control unit is arranged to provide the nominal energy level in a pulse width modulation manner.

9. The personal hygiene device in accordance with claim 1, further comprising a pressure detection unit for determining the pressure exerted against a functional head of the personal hygiene device and the control unit is arranged to reduce the energy level provided at the drive unit by a predetermined amount during a pressure reduction time period if a determined pressure is above a first pressure threshold.

10. A method of controlling a personal hygiene device having a drive unit, an energy storage, and a control unit, the method comprising the steps of:
   changing the personal hygiene device from an off state into an on state;
   repeatedly or constantly determining the energy storage level of the energy storage;
   gradually reducing an energy level provided at the drive unit from a nominal energy level to a first reduced energy level during a first energy level reduction time period if the determined energy storage level falls below a first energy storage level threshold but is above a second energy storage level threshold; and continuingly providing the first reduced energy level while the personal hygiene device stays in the on state and the determined energy storage level stays above the second energy storage level threshold, the method comprising directly providing the first reduced energy level at the drive unit when a switch-off time period of the drive unit has been lower than a first switch-off time period threshold and the first reduced energy level had been provided at the drive unit in the preceding on-state of the personal hygiene device, wherein the first switch-off time period threshold is below 30 seconds.

11. The method in accordance with claim 10, comprising gradually reducing the energy level provided at the drive unit from the nominal energy level to the first reduced energy level during a second energy level reduction time period effectively immediately after changing the personal hygiene device from the off state into the on state if the determined energy storage level is above the second energy storage level threshold when the first reduced energy level had been provided in the preceding on-state of the personal hygiene device and a charging of the energy storage had not happened.

12. The method in accordance with claim 10, comprising gradually reducing the energy level provided at the drive unit from the first reduced energy level to a second reduced energy level or zero energy level during a third energy level reduction time period when the determined energy storage level is below the second energy storage level threshold.

* * * * *